United States Patent [19]

Casey

[11] Patent Number: 5,766,005
[45] Date of Patent: Jun. 16, 1998

[54] WIRE END PROTECTION CAP ASSEMBLY

[76] Inventor: Kevin M. Casey, 17722 Loop Rd., Holt, Mo. 64048

[21] Appl. No.: 824,618

[22] Filed: Mar. 27, 1997

[51] Int. Cl.$^6$ .................................................. A61C 3/00
[52] U.S. Cl. .................................................. 433/15; 433/22
[58] Field of Search ........................... 433/2, 5, 15, 20, 433/22; 24/26, 27, 28, 29

[56] References Cited

U.S. PATENT DOCUMENTS

| | | | |
|---|---|---|---|
| 1,898,212 | 2/1933 | Polcini | 24/128 |
| 1,938,428 | 12/1933 | Johnson | 433/22 |
| 2,592,696 | 4/1952 | Hoody | 24/115 F |
| 4,262,391 | 4/1981 | Peash | 24/27 |
| 4,708,646 | 11/1987 | Jasper | 433/22 |
| 4,797,094 | 1/1989 | Karwoski | 433/22 |
| 4,867,679 | 9/1989 | Rackley | 433/15 |
| 5,160,260 | 11/1992 | Chang | 433/2 |
| 5,433,088 | 7/1995 | Mahar | 24/27 |

*Primary Examiner*—John J. Wilson
*Attorney, Agent, or Firm*—Shook, Hardy & Bacon L.L.P.

[57] ABSTRACT

A cap assembly is provided for use on an oral ligature wire presenting ends that are twisted together. The cap assembly protects the oral tissue surrounding the twisted wire ends from abrasion, and includes a cap 22, 30, 36, 50, 60 sized for receipt over the twisted wire ends. The cap is formed of a material that is soft relative to the wire so that it defines a physical barrier between the twisted wire ends and the surrounding oral tissue. A collar is defined by or secured to the cap and is sized for receipt on the wire for retaining the cap on the wire while the wire ends are twisted and the cap is manipulated into covering relation on the wire ends.

14 Claims, 2 Drawing Sheets

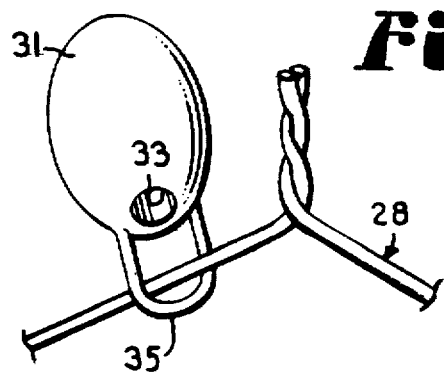
Fig. 9.
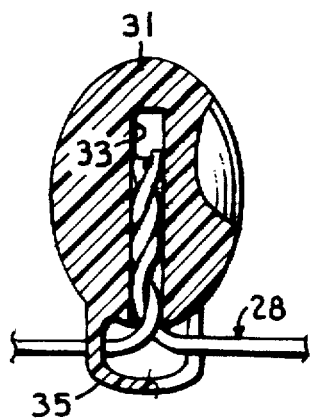
Fig. 10.
Fig. 11.
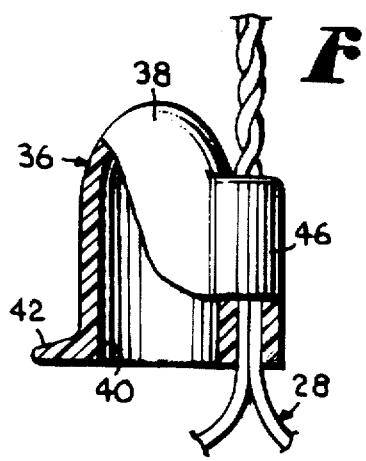
Fig. 12.
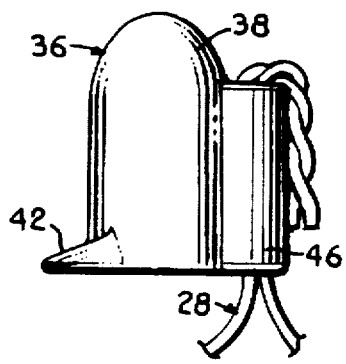
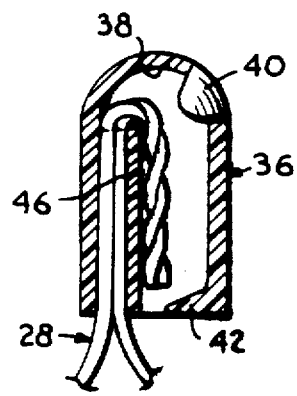
Fig. 13.
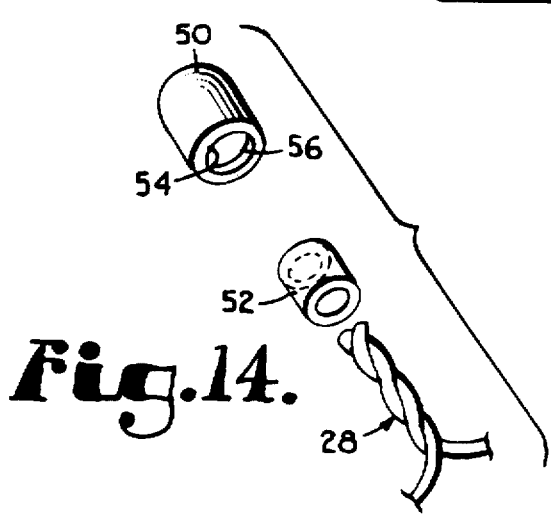
Fig. 14.

WIRE END PROTECTION CAP ASSEMBLY

BACKGROUND OF THE INVENTION

The present invention relates generally to the art of dentistry, and more particularly to a cap assembly that is used to cover and protect the twisted ends of a ligature wire so that the wire ends do not cut or abrade the surrounding oral tissue.

It is a conventional practice to secure an orthodontic appliance in the mouth of a patient by tying the appliance to one or more of the patient's teeth with ligature wires. Typically, each ligature wire is formed of a malleable material that can be easily wrapped around a tooth and the appliance, and presents opposed axial ends that are brought together and twisted to secure the wire in place. Although the malleability of the wire permits the twisted wire ends to be tucked between teeth or against the gum of the patient, there remains a tendency for the ends to collect debris and to abrade the oral tissue surrounding the ligature wire. Wax can be deposited on the wire ends to reduce the abrasion caused by the wire ends. However, the wire ends have a tendency of pushing through the wax over time, necessitating the need for additional wax, and the accumulation of wax in and around the fixture creates its own problems known to those of skill in the art.

SUMMARY OF THE INVENTION

It is an object of the present invention to provide a cap assembly that is used to cover and protect the twisted ends of a ligature wire so that debris does not collect on the twisted ends, and so that the wire ends do not cut or abrade the oral tissue surrounding the ligature wire.

It is another object of the invention to provide a cap assembly that can be positioned on a ligature wire and then manipulated after twisting of the wire ends to quickly cover and protect the ends.

In accordance with these and other objects evident from the following description of a preferred embodiment of the invention, a cap assembly is provided for use on a ligature wire presenting ends that are twisted together. The cap assembly protects the oral tissue surrounding the twisted wire ends from abrasion, and includes a pocket sized for receipt over the ends and a collar for retaining the pocket on the wire. The pocket is formed of a material that is soft relative to the wire so that it defines a physical barrier between the twisted wire ends and the surrounding oral tissue. The collar is secured to the pocket, and is sized for receipt on the wire for retaining the pocket on the wire while the wire ends are twisted together. Once tying of the ends is complete, the pocket is then manipulated into position covering the ends.

By providing an assembly in accordance with the present invention, numerous advantages are realized. For example, by providing a cap assembly presenting a pocket that can be manipulated to cover the twisted ends of a ligature wire, it is possible to protect the wire ends against cutting or abrading surrounding oral tissue, and debris is not allowed to become lodged within the twisted ends. In addition, the cap assembly presents a relatively clean appearance.

BRIEF DESCRIPTION OF THE DRAWING

The preferred embodiment of the present invention is described in detail below with reference to the attached drawing figures, wherein:

FIG. 9 is a perspective view of a cap assembly constructed in accordance with a third preferred embodiment;

FIG. 10 is a sectional view of the cap assembly shown in FIG. 9, illustrating placement of the cap assembly over the twisted wire ends;

FIG. 11 is a side elevational view, partly in section, of a cap assembly constructed in accordance with a fourth preferred embodiment;

FIG. 12 is an elevational view similar to FIG. 11, illustrating folding of the twisted wire ends;

FIG. 13 is a sectional view of the cap assembly shown in FIG. 11, illustrating manipulation of the cap assembly into a position covering the twisted and folded wire ends; and FIG. 14 is a perspective view of a cap assembly constructed in accordance with a fifth preferred embodiment;

DETAILED DESCRIPTION OF THE PREFERRED EMBODIMENT

Five different cap assemblies constructed in accordance with the preferred embodiment of the present invention are illustrated in FIGS. 1, 5, 9, 11 and 14. The construction and method of use of each of the preferred assemblies is described in detail below.

Figure 1:
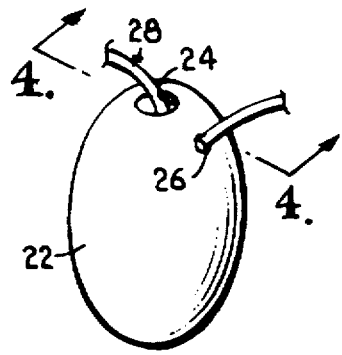
FIG. 1 is a perspective view of a wire end protection cap assembly constructed in accordance with the preferred embodiment.

The first embodiment of the cap assembly is illustrated in FIG. 1, and includes a solid unitary cap 22 of generally spherical or elliptical shape, formed of a resilient, compressible material such as rubber or an elastomeric material. The cap includes a radial first bore 24 extending into the cap from the exterior surface thereof which defines a pocket sized for receipt over the twisted wire ends of a ligature wire. A smaller second bore 26 communicates with the pocket and defines a collar that is sized for receipt on the ligature wire for retaining the cap on the wire during twisting of the wire ends.

Figure 2:
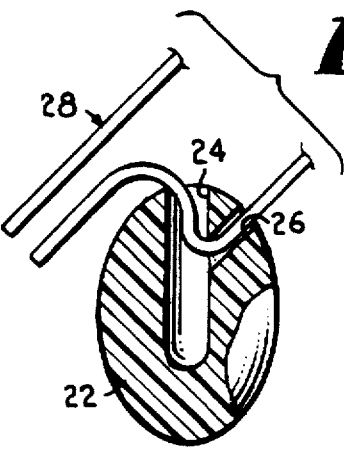
FIG. 2 is a sectional view of the cap assembly illustrating placement of the assembly on a ligature wire.
Figure 3:
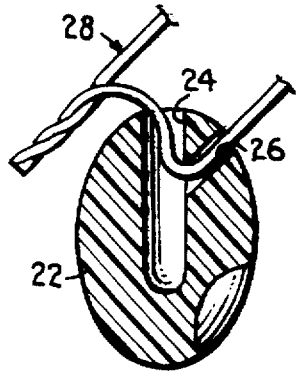
FIG. 3 is a sectional view similar to FIG. 2, illustrating placement of the assembly during twisting of the wire ends.
Figure 4:
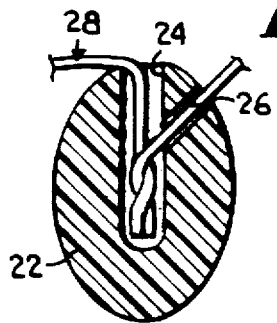
FIG. 4 is a sectional view similar to FIG. 2, illustrating manipulation of the cap assembly into a position covering the twisted wire ends.

As shown in FIG. 2, when a ligature wire 28 is to be used in fastening a dental appliance to the teeth of a patient, the wire is threaded first through the smaller second bore 26 of the cap and out the first bore 24 so that the cap can be slid along the length of the wire out of the way of the dentist or oral surgeon. Once the wire ends have been twisted together to secure the appliance in place, as shown in FIG. 3, the cap is slid back into proximity with the twisted ends, and is pulled over the ends so that they are received in the pocket, as illustrated in FIG. 4. As such, the relatively soft material of the cap protects the surrounding tissue from abrasion and shields the twisted ends of the ligature wire from exposure to debris.

As an alternative to forming the cap with a pocket, it is possible provide a cap having only a bore extending through the cap for allowing placement of the cap on a pair of twisted wire ends. In such a construction, the wire ends are twisted together and then forced back into the cap, e.g. by puncturing the material of the cap, to provide a physical barrier between the wire ends and the surrounding oral tissue. As such, a pocket is defined by the body after being pierced by the twisted wire ends upon completion of a tying operation.

Figure 5:
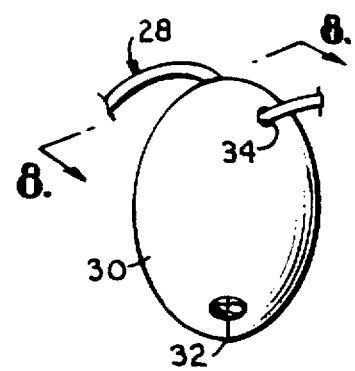
FIG. 5 is a perspective view of a cap assembly constructed in accordance with a second preferred embodiment.
Figure 6:
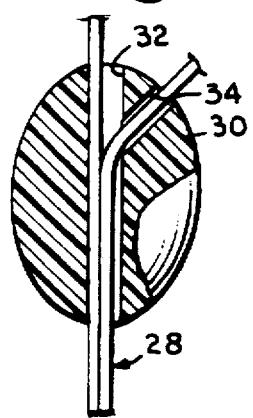
FIG. 6 is a sectional view of the cap assembly shown in FIG. 5, illustrating placement of the assembly on a ligature wire prior to twisting of the wire ends.

A cap assembly constructed in accordance with the second embodiment is illustrated in FIG. 5, and includes a solid unitary cap 30 of generally spherical or elliptical shape, formed of a resilient, compressible material such as rubber or an elastomeric material. As shown in FIG. 6, the cap includes a radial first bore 32 extending completely through the cap and defining an open-ended pocket sized for receipt over the twisted wire ends of a ligature wire. As with the first embodiment, a smaller second bore 34 communicates with the first bore and defines a collar that is sized for receipt on the ligature wire 28 for retaining the cap on the wire during twisting of the wire ends.

Figure 7:
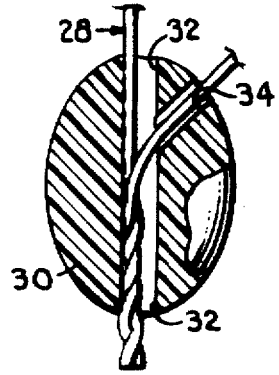
FIG. 7 is a sectional view similar to FIG. 6, illustrating twisting of the wire ends.
Figure 8:
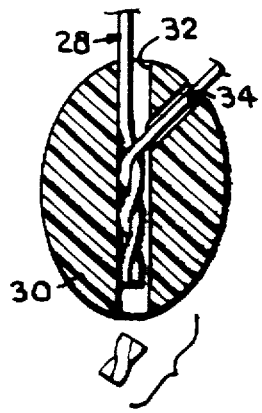
FIG. 8 is a sectional view similar to FIG. 6, illustrating the final position of the assembly covering the twisted wire ends.

During use, the ligature wire ends are threaded through the bores 32, 34 of the cap and out the end of the first bore 32 so that the ends of the wire can be twisted, as illustrated in FIG. 7. If the wire ends protrude completely through the cap, the cap is pinched or compressed longitudinally of the first bore 32, exposing more of the twisted ends than would otherwise protrude from the cap. Conventional wire cutters are employed to clip the exposed wire material, as shown in FIG. 8, so that when the cap is released and allowed to return to its uncompressed condition, the wire ends are completely shielded by the cap 30. As such, the relatively soft material of the cap protects the surrounding tissue from abrasion and shields the twisted ends of the ligature wire from exposure to debris.

As an alternative to the use of a rubber or elastomeric material, it is possible to form the cap of nylon or the like, which can be crimped or deformed by a tool once placed over the wire ends. When nylon is used, the method of using the cap differs slightly from the method described with reference to the illustrated embodiment in that it is not necessary to pinch or compress the first bore 32 before cutting the wire ends. Instead, once the wire ends are twisted together, the cap is deformed to cover the exposed tips of the wire ends, protecting the surrounding tissue from abrasion. Because the material of the cap does not return to its original shape after being deformed, it covers the wire ends without further manipulation.

Although the cap 22 is illustrated as being a spherical or elliptical body having first and second bores defining the pocket and collar, it is understood that the collar could be formed by a strap or the like, as shown in FIG. 9, presenting opposed ends that are secured to the pocket to provide the same advantageous functions as the illustrated construction. In the embodiment illustrated in FIG. 9, the cap 31 is of generally spherically or elliptical shape, and is formed of a resilient, compressible material such as rubber or the like. The cap includes a radial bore 33 extending into the cap from the exterior surface thereof and defining a pocket sized for receipt over the twisted wire ends of a ligature wire. The strap 35 is formed of the same material as the cap 31, and includes opposed axial ends that are secured to the cap to hold the strap in place.

During use of the cap assembly shown in FIG. 9, the strap is trained over an end of the ligature wire 28, and the ligature wire ends are twisted together. Thereafter, the cap 31 is brought over the twisted ends of the wire and is prevented from coming free from the twisted ends by the strap 35, as shown in FIG. 10.

The fourth embodiment of the cap assembly is shown in FIG. 11, and includes a solid unitary cap 36 formed of a resilient, compressible material such as rubber or an elastomeric material. The cap includes a relatively thin walled pocket presenting an opening, an interior surface 38, and an exterior surface 40. A flange 42 extends around and defines the opening of the pocket, and is of a thickness greater than that of the remainder of the pocket so that the flange retains its shape after the pocket is manipulated in use.

A relatively thick-walled tubular sleeve 46 is secured along its length to the interior surface of the pocket and presents a first opening adjacent the opening of the pocket. The opposite end of the sleeve opens adjacent the closed end of the pocket. The sleeve defines a collar that is sized for receipt on the ends of the ligature wire for retaining the cap on the wire during twisting of the ends.

The first step in using the cap 36 is to thread the wire ends of the ligature wire 28 through the sleeve 46 after the wire has be wrapped around the appliance and tooth that are to be secured together. During this placement of the cap assembly, the pocket is oriented as shown in FIG. 11, with the interior surface 38 facing outward and the exterior surface 40 facing inward. Once the wire ends have been threaded through the sleeve 46, they are twisted together to secure the appliance in place, and are then folded over against the side of the sleeve, as shown in FIG. 12, to hold the sleeve in place and prevent it from being pulled from the ligature wire. Thereafter, the pocket is gripped by the flange 42 and is inverted so that the pocket is received over the twisted wire ends and the sleeve, as illustrated in FIG. 13, protecting the wire ends from exposure to debris and shielding the surrounding tissue from abrasion. As such, the interior surface 38 of the pocket faces inward toward the twisted ends and the sleeve, and the exterior surface 40 faces outward. The flange 42 of the pocket is resilient enough to permit this reversible inversion of the pocket relative to the sleeve, while providing a tight fit of the pocket over the sleeve and wire ends.

Turning to FIG. 14, the fifth construction of the preferred embodiment is illustrated as including a cap 50 and a collar 52 that are preferably each formed of a resilient, compressible material such as rubber or elastomeric material. It is also possible to form the cap 50 and/or collar 52 out of nylon or the like, or to taper the collar toward the distal end thereof to faciltate placement of the cap over the collar. The cap is generally cup-shaped and includes a radial bore 54 extending into the cap from the exterior surface thereof for defining a pocket sized for receipt over the collar. A relatively thick flange 56 is be provided adjacent the bore and presents a lip, if desired, for facilitating handling of the cap. The collar 52 is a tubular sleeve presenting a longitudinal bore sized for receipt on the ends of a ligature wire, and can be positioned on the wire ends either before or after twisting of the wire.

When a ligature wire 28 is used, the wire is threaded first around the tooth and the appliance that are to be secured together, and the ends are then twisted together to secure the appliance in place. The collar 52 is slid over the twisted ends, and the ends are folded over to prevent the collar from sliding off of the wire ends. The cap 50 is then pulled over the collar 52 and folded wire ends so that the collar is completely received within the pocket. The flange 56 stretches to permit this receipt of the collar and ligature wire, and returns toward a relaxed condition once the pocket is in place. Preferably, the inner diameter of the flange 56 in the relaxed condition is smaller than the outer diameter of the collar 52 so that the flange closes partially over the end of the collar upon assembly, preventing the cap 50 from being too easily removed. As such, the relatively soft material of the cap and collar protects the surrounding tissue from abrasion and shields the twisted ends of the ligature wire from exposure to debris.

Although the present invention has been described with reference to the preferred embodiment, it is noted that equivalents may be employed and substitution made herein without departing from the scope of the invention as recited in the claims.

What is claimed is:

1. A cap assembly for use on an oral ligature wire presenting ends that are twisted together, the cap assembly protecting the oral tissue surrounding the twisted wire ends from abrasion, and comprising:

a cap presenting a pocket sized for receipt over the twisted wire ends, the cap being formed of a material that is soft relative to the wire to define a physical barrier between the twisted wire ends and the surrounding oral tissue; and a collar secured to the cap and sized for receipt on the wire for retaining the cap on the wire.

2. A cap assembly as recited in claim 1, wherein the cap and the collar are formed of a unitary piece of elastomeric material.

3. A cap assembly as recited in claim 1, wherein the cap and the collar are formed of a unitary piece of rubber.

4. A cap assembly as recited in claim 1, wherein the cap defines a longitudinal axis along which the pocket extends, the cap being compressible along the length of the axis so that the cap can be retracted relative to the wire ends in the pocket, allowing the wire ends to be clipped.

5. A cap assembly as recited in claim 1, wherein the collar is defined by a bore extending into the cap and communicating with the pocket.

6. A cap assembly as recited in claim 1, wherein the cap presents an opening to the pocket, and includes a lip extending around at least a portion of the opening so that the cap may be manipulated relative to the collar.

7. A cap assembly as recited in claim 1, wherein the collar is tubular and is affixed to the cap.

8. A cap assembly as recited in claim 1, wherein the collar is tubular and is a separate element from the cap.

9. A cap assembly as recited in claim 1, wherein the collar is defined by a hole formed in the side of the cap and by which the cap is received on the wire.

10. A cap assembly as recited in claim 1, wherein the cap is invertible between an inside-out position in which the collar is disposed outside the pocket and is accessible for guiding the collar onto the wire, and an inside-in position in which the collar and wire ends are enveloped within the pocket.

11. A cap assembly for use on a pair of oral ligature wire presenting ends that are twisted together, the cap assembly protecting the oral tissue surrounding the twisted wire ends from abrasion, and comprising:

a collar sized for receipt on the twisted ends of the ligature wire;

a cap defining a pocket sized for receipt over the collar and the twisted wire ends, the cap being formed of a material that is soft relative to the wire so that the cap defines a physical barrier between the twisted wire ends and the surrounding oral tissue; and a means for securing the cap to the collar upon fitting of the cap over the collar to secure the cap in place over the collar.

12. A cap assembly as recited in claim 11, wherein the cap and the collar are formed of a unitary piece of elastomeric material.

13. A cap assembly as recited in claim 11, wherein the cap and the collar are formed of a unitary piece of rubber.

14. A cap assembly as recited in claim 11, wherein the cap presents an opening to the pocket and includes a lip extending around at least a portion of the opening so that the cap may be manipulated.

* * * * *